United States Patent [19]

Rippstein, Jr.

[11] 4,447,413

[45] May 8, 1984

[54] DRIFT INFLUENCING COMPOSITION

[75] Inventor: Wayland J. Rippstein, Jr., Alvin, Tex.

[73] Assignee: Aviation Chemical, Inc., Winnie, Tex.

[21] Appl. No.: 284,192

[22] Filed: Jul. 17, 1981

Related U.S. Application Data

[63] Continuation-in-part of Ser. No. 147,721, May 8, 1980, abandoned.

[51] Int. Cl.³ .......................................... A61K 31/74
[52] U.S. Cl. ..................................................... 424/78
[58] Field of Search .......................................... 424/78

[56] References Cited

U.S. PATENT DOCUMENTS 3,360,356 12/1967 Vartiak ................................. 71/65
3,934,005 1/1976 Albert .................................. 424/78

OTHER PUBLICATIONS

Chem. Abst. 76, 142,712(6), (1972)–Kishi et al.
Air Drop–Drift Control Additive–by–Knapp Chem. Co.
Target–Drift Reduction Agent–Loveland Industries.
Polyox–Water Soluble Agents–Union Carbide, pp. 1-10.
Water Soluble Resins are Unique–Union Carbide.
Ethylene Oxide Polymers,–Union Carbide.
Chapter 19, Polyethylene Oxide–Handbook of Water-Soluble Gums and Resins.

*Primary Examiner*—Douglas W. Robinson

[57] ABSTRACT

A drift influencing composition for use with agricultural chemicals for aerial distribution to farm crops or the like comprising a quantity of water soluble friction reducing resin, high molecular weight (300,000 to 4,000,000) polyethylene oxide in solution with water in the concentration range of 70 parts per million by weight to 200 parts per million by weight to retard the drift of aerial sprayed agricultural chemicals, and in the concentration range of one-half parts per million by weight to 70 parts per million by weight to enhance the drift of aerial sprayed agricultural chemicals, which functions to reduce surface tension of the solution and enhance efficient aerial spraying and providing sufficient coagulation to minimize wind induced drift.

4 Claims, 3 Drawing Figures

DRIFT INFLUENCING COMPOSITION

This is a continuation-in-part of application Ser. No. 147,721, filed May 8, 1980.

FIELD OF THE INVENTION

This invention relates generally to spray droplet size control primarily for aerial chemical distributions such as is used, for example, in the spraying of agricultural chemicals onto crops from an aircraft. More specifically, the teaching of the present invention is intended to relate both to an agent for reducing drift, such as for the aforementioned purpose, and which may alternatively be used for enchancing drift of aerially sprayed chemicals either, alternatively, by selective adjustment of the concentration so as to influence the viscosity and surface tension of the liquid which is thereafter mixed with the chemical to be distributed. Since drift retardance is a more prevalent objective in commerce and agriculture, the invention will hereafter be demonstrated principally with respect to that objective, rather than drift enhancement.

BACKGROUND OF THE INVENTION

In order to enchance the yield rate of many farm crops, it is desirable to apply various chemical compositions to the drops at different stages of growth thereof. For example, liquid or granulated chemical fertilizers are distributed aerially in order to stimulate growth and development of certain crops. To prevent the crops from being damaged by insect life, fungus and various other damaging factors, it may be desirable to also spray the crops with pesticides (insecticides, fungicides or herbicides) in either liquid or wettable power form. Further, in the case of certain crops such as cotton, for example, where controlled defoliation is desired, aerial spraying is again utilized in order to spray the crops with liquid defoiliant materials.

Where aerial sraying, as well as liquid spraying of other character, is accomplished, it is highly desirable that the liquid material being sprayed fall directly on the crops being sprayed and that wind induced drifting of the sprayed liquid material be eliminated or at least substantially retarded. In the event of substantial quantity of the sprayed particulate is of sufficiently minute size as to be readily entrained in the air and under circumstances where even slight air movement is occurring, the chemical material can be induced to drift with the moving air onto adjacent land where it may be detrimental to plant and/or animal life. It is desirable to provide the agricultural chemcial being sprayed or distributed with a drift influencing composition so that the particulate or spray droplets will be relatively large when distributed and will readily settle out of the air onto the plant life rather than drift away with any prevailing winds that may be present at the time of spraying.

In general, providing agricultural chemicals to be sprayed with thickners to increase the spray solution viscosity to retard drift causes other problems. Namely, higher pumping pressures will be required in order to achieve relatively efficient distribution and these higher pump pressures develop problems from the standpoint of maintenance and repair of the pumping and liquid distribution epuipment typically provided for aerial spraying. Also, higher viscosities cause undesirable plugging of the spray nozzles and a marked decrease in volume of spray solution per unit of time. It is desirable, therefore, to provide a drift influencing composition having good droplet size control qualities for drift control and yet having miminal friction characteristics in order that efficient pumping and spraying distribution may be accomplished a nominal pump pressures.

When farm crops are being sprayed with agricultural chemicals, it is also highly desirable to provide agricultural chemical materials that may be easily handled and may also be prepared in a remote field environment such as the remote landing strips that are typically utilized by agricultural airplanes for crop spraying operations. It is desirable, therefore, to provide a drift retardant composition that may be simply and efficiently transported to such remote facilities in a liquid form of proper concentration and may be simply and efficiently mixed with the agricultural chemicals in order to develop a liquid agricultural chemical composition for immediate loading into the chemical tanks of the airplanes for spraying operations.

In the alternative, it may be desirable to enhance the drift of aerially sprayed chemicals such as in fumigation programs where it is desirable to cover large areas with the agricultural chemical sprayed. It is therefore desirable to provide a drift influencing composition which will enchance the drift of aerially sprayed agricultural chemicals.

SUMMARY OF THE INVENTION

It is a primary feature of this invention to provide a novel drift influencing composition having efficient drift retardant characteristics to prevent airborne spray particulate from wind drifting to an undesirable degree and also in the alternative to have said drift influencing composition to provide efficient drift enhancing characteristics by merely changing the concentration level of said composition.

It is an even further feature of this invention to provide a novel drift retardant liquid for agricultural chemicals which is low in cost, non-toxic in use and which may be simply and efficiently prepared in a field environment such as at remote landing strips for agricultural crop spraying airplanes.

Basically, the above noted features and objects of the present invention are accomplished by providing a drift influencing composition which may be efficiently delivered in easily handled containers to remote sites such as landing strips for agricultural airplanes, farm crop areas, etc. Water may be provided in any suitable manner at the remote site and agricultural chemicals may also be provided at the remote site. The drift influencing composition is simply mixed in the proper concentration to be used for either retarding drift or enhancing drift with suitable quantities of the agricultural chemical. Only a few minutes of mixing is required in order to achieve efficient dispersion of the drift retardant liquid within the agricultural chemical.

Of a more specific nature, the drift influencing composition is defined by a water soluble friction reducing resin such as a high molecular weight polyethylene oxide (average molecular weight in the range of 300,000 to 4,000,000) in solution with water in the concentration range of 70 parts per million to 200 parts per million by weight for drift retardance, and in the concentration range of one-half (½) ppm to 70 ppm by weight for drift enhancement.

Other and further objects, advantages and features of the invention will become obvious to one skilled in the art upon an understanding of the illustrative embodiment about to be described, and various advantages, not referred to herein, will occur to one skilled in the art upon employment of the invention in practice.

DETAILED DESCRIPTION OF THE PREFERRED EMBODIMENT

The water soluble resin material may conveniently take the form of water soluble ethylene oxide polymer such as that manufactured by the Union Carbide Corporation and sold under the registered trademark POLYOX and preferably Polyox WSR-301. Specifically, the polyethylene oxide may be provided in powdered form and may be mixed with water in concentrations of from 70 ppm to 200 ppm by weight ratio to provide efficient drift retarding characteristics. The water soluble resin material is granular linear nonionic polyethylene oxide homopolymers in the range of an average molecular weight of 300,000 to an average molecular weight of 4,000,000 (300,000–4,000,000) and in a water solution, even in very small concentration such as the range of concentration described above, exhibit significant capabilities to function efficiently as a drift retardant. Being polyethers, these resins hydrogen bond strongly with water which accounts for their solvation by water.

Manufacturers of agricultural pesticides usually market and sell their pesticides in wettable powder form. The wettable powders when mixed with aqueous solutions have a tendency to coagulate and not remain in suspension when used with polyethylene oxide resin with molecular average weights greater than 4,000,000. It is therefore important to restrict the average molecular weight of the polyethylene oxides to the range of 300,000 to 4,000,000 to prevent the coagulation of the wettable powders in the pesticides used. This will ensure that the wettable powders remain in suspension for suitable spraying operations.

Another unusual characteristic of polyethylene oxide is its capability to significantly increase the viscosity of both dilute and concentrated aqueous solutions. Polyethylene oxide resins have been found to function quite efficiently as a liquid agricultural chemical spray retardant because of its complete water solubility, high thickening efficiency and because of its high resistance to biological attack. Moreover, the ease by which polyethylene oxide resins are capable of being mixed with various liquid materials enhances the capability of its utilization in transportation to remote sites and subsequent on-site mixing in an outdoor or field environment such as at remote agricultural aircraft landing sites.

As mentioned, it has been found that the addition of polyethylene oxide affects the basic physical properties of water by increasing its viscosity and decreasing its surface tension, which has a direct result on the average mean diameter size of droplets. The average mean diameter size of droplets is affected by surface tension and viscosity. In general, as the surface tension decreases, the average mean diameter size of droplets also decreases. Also, as the viscosity increases, the average mean diameter size of droplets increases.

Figure 1:
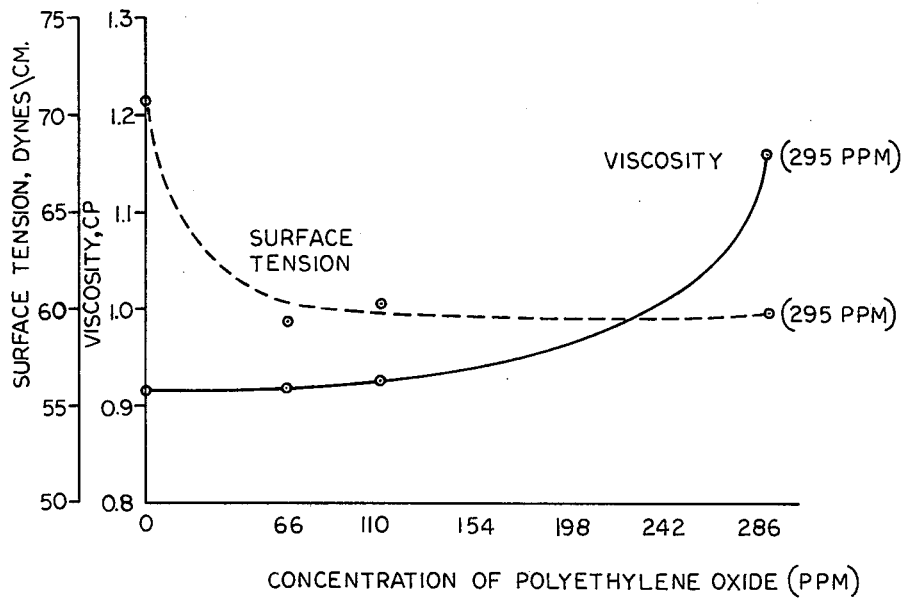
FIG. 1 shows the effect of polyethylene oxide concentration on static surface tension and viscosity.

FIG. 1 illustrates the relationship of surface tension and viscosity with regard to the concentration levels of polyethylene oxide. Referring to FIG. 1, it is noted that as to concentration of polyethylene oxide increases, the surface tension decreases, but the viscosity increases. The viscosity measurements indicated a noticably effect (26% increase) at the 295 ppm concentration. As can be seen from FIG. 1, the addition of polyethylene oxide in excess of 295 ppm by weight drastically increases the viscosity. To avoid the problems as mentioned above associated with high viscosity, the concentration of polyethylene oxide must be limited at the upper range of 200 ppm by weight to be used as an efficient and effective drift retardant.

Figure 2:
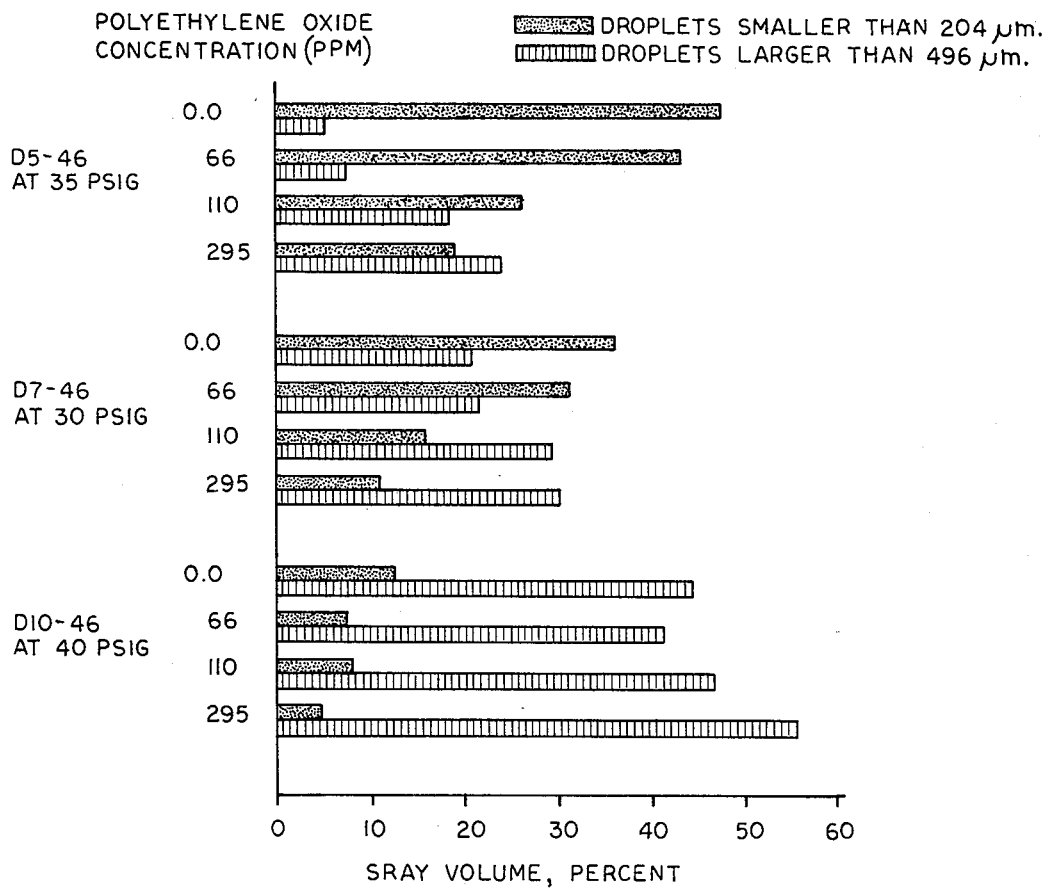
FIG. 2 shows the percentage of spray volume in spray droplets smaller than 240 microns and larger than 496 microns.

In addition, it was found that the addition of polyethylene oxide to water created a discernable shift in the droplet size distribution. It was found that the addition of polyethylene oxide reduces the percentage of spray volume composed of small droplets and increases the maximum mean droplet size diameter formed. This is dramatically shown in FIG. 2. Three different disc core hollow cone spray nozzles were used. It was found that for each nozzle, the percentage of spray volume in droplets smaller than 204 microns decreased as the concentration of polyethylene oxide was increased. The percentage of spray volume in droplets smaller than 204 microns was reduced approximately sixty to seventy percent for all three nozzles when used in the 295 ppm by weight concentration of polyethylene oxide, as compared to no polyethylene oxide. Increase in the concentration of polyethylene oxide caused an increase in the maximum mean droplet size. The percentage of spray volume contained in droplets with mean diameters larger than 496 microns is also shown in FIG. 2. This comparison illustrates the consistent increase in droplet size as to concentration of polyethylene oxide is increased.

Figure 3:
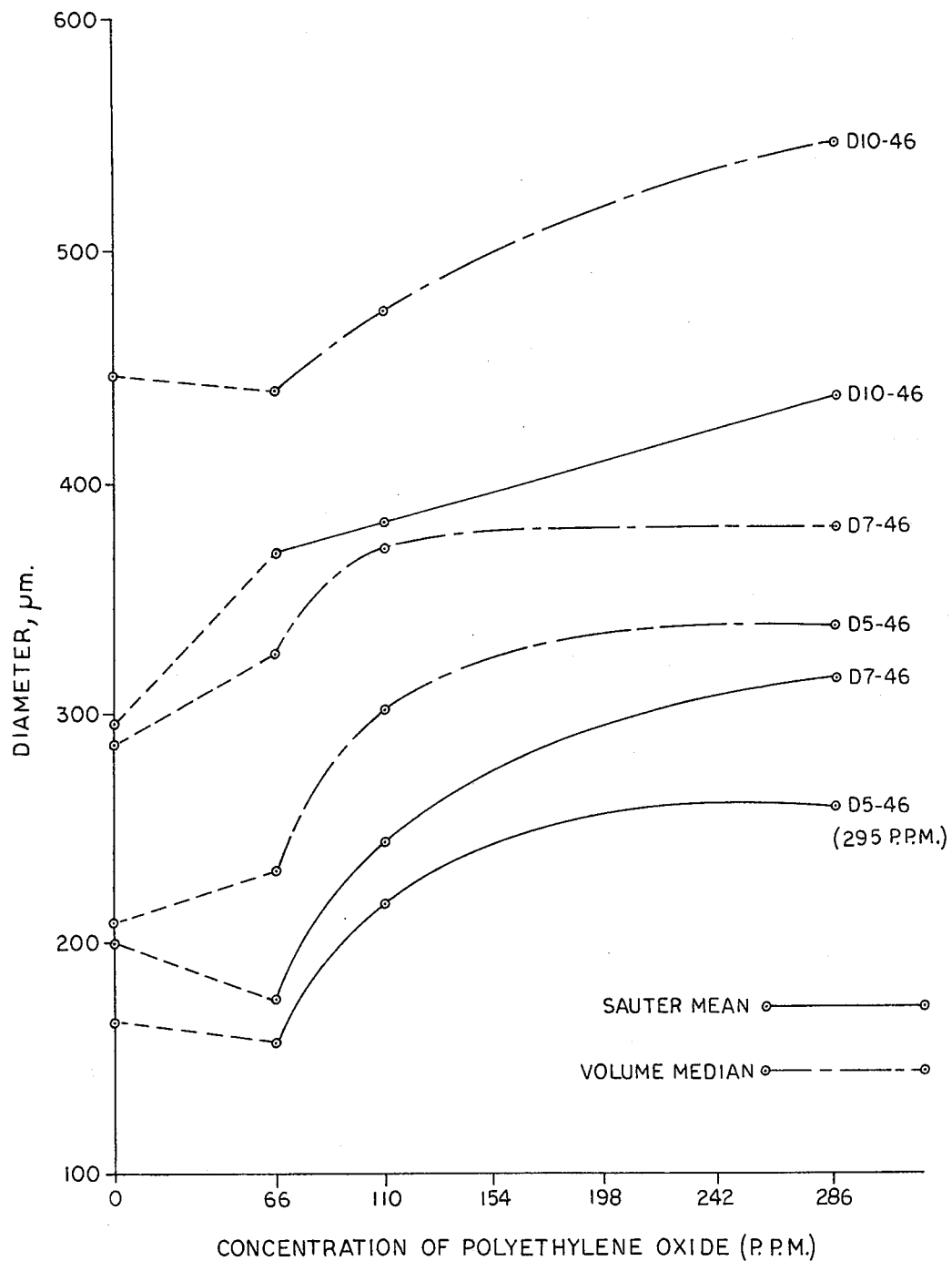
FIG. 3 shows the effect of polyethylene oxide on the Sauter Mean and Volume Median diameters.

Both reduction in small droplets and the increase in the maximum droplet size caused the means and medians of the droplet size distributions to increase with increased concentrations of polyethylene oxide. The "Volume Median diameter" and the "Sauter Mean diameter" are two statistics typically used to describe droplet size. The relationship between these statistics and polyethylene oxide concentration for the nozzle used is shown in FIG. 3. An important point which was discovered, and is a part of this invention, is the effect of polyethylene oxide concentrations less than 70 ppm by weight which is a point of major interest with regard to drift enhancement. It was found that concentrations of polyethylene oxide less than 70 ppm by weight produced an actual decrease in the Sauter Mean and Volume Mean droplet size. Although it is not known why this happens, it is believed that this results from the sharp reduction in liquid surface tension created by small concentrations of polyethylene oxide without the balancing effect of increased viscosity which results at higher concentrations. FIG. 3, in conjunction with FIG. 1, shows the overall effect of the concentration range. As mentioned, when the concentration of polyethylene oxide exceed 200 ppm by weight, there is no significant change on the Sauter Mean or Volume Median diameter size of the droplets (FIG. 3). In fact, when the concentration exceeds 200 ppm by weight, the viscosity drastically increases (FIG. 1) and as the concentration increases beyond 200 ppm, the mean diameter of the droplets, due to the increase in viscosity, will approach and become the diameter of the nozzle jet, and thus exit the nozzle jet as a solid stream of atomized water. Therefore, the concentration of 200 ppm is the upper limit for effective drift retardance. Below concentrations of 70 ppm by weight droplet sizes become smaller than water itself due to the decrease in the Sauter Mean and Volume Median, and the reduced surface tension without the balancing effect of increased viscosity.

It has thus been discovered, and is the subject of this invention, that the optimum concentration range for the molecular weight polyethylene oxide, as disclosed herein, to be used as a drift retardant when mixed with water, is in the range of 70 ppm by weight to 200 ppm by weight and that the optimum concentration range for the molecular weight polyethylene oxide, as disclosed herein, to be used as a drift enhancer when mixed with water, is in the range of one-half ($\frac{1}{2}$) ppm by weight to 70 ppm by weight.

In order to illustrate the concept of the drift influencing composition as a drift retardant, according to the present invention, the following tests were performed and are set forth in exemplary form as follows:

I. Equipment:
  A. Aircraft: Grumman Model G 164 A-600 hp engine with 300 gallon hopper
  B. Pump: Wind driven with brake-screen pump outlet and booms
  C. Spray Booms: A total of 36 standard Delivan #LF 10 T jet nozzles mounted to front of lower wing, set downward and 45° to rear. (Droplets issued are medium course)
  D. Test Blocks: 4 in. sq. (104 cm$^2$) wooden blocks covered with Kodak Linagraph paper #480 (water sensitive)

II. Testing Procedures:
  A. All spray tests were conducted in 90° crosswinds.
  B. Air speed: 100 mph
  C. Power Setting: 29 in. of manifold pressure
  D. R.P.M.: 1950
  E. Flow rate: 32 gal. per min.-4 gal. per acre
  F. Pump Pressure: Pressure was raised from 20 psi to 40 psi so that a greater amount of spray could be induced into the atmosphere, thus allowing more droplets giving a better reading on test blocks.
  G. Spray Release: Spray valve was opened 200 ft. before and after passage over test area. Altitude was approximately 6 ft. above ground.
  H. Materials Used: An equeous solution at a concentration of polyethylene oxide in water at 400 ppm by weight.
  I. Test Block Settings: A total of 50 test blocks were placed in a straight line 160 ft. long. This line was 90° to flight of aircraft. Blocks extended 80 ft. on either side of center line of swath sprayed by aircraft. After each spray test run of aircraft, test paper was numbered and inspected for spray pattern and random finds. New paper was used for each spray test run.

TEST I

Weather-Adverse overcast sky
Wind-Gusting between 7-12 mph
Humidity-87°
Time-9:00 a.m.-10:40 a.m.
Note-Weather conditions remained the same during entire period of spray test runs.

I. First Run:
  A. Aircraft hopper was charged with water
  B. Test blocks were set
  C. All flight test procedures were complied with
  D. Test flight spray pattern was applied
  E. Results:
    1. Vortex tip-roll cam up over top wing
    2. Downwind drift was in excess of 350 ft.
    3. Test blocks indicated that spray pattern was erratic and scattered—in many cases streaked
    4. Size of finds ran from 1.2 cm$^2$–0.01 cm$^2$
    5. An exact count of droplets and finds was taken from test blocks
  F. End of first run, first test, hopper drained, paper changed.

II. Second Run:
  A. Aircraft hopper was charged with an aqueous solution at a concentration of polyethylene oxide in water at 200 ppm by weight.
  B. Test blocks were set
  C. All flight test procedures were complied with
  D. Test flight spray pattern was applied
  E. Results:
    1. Vortex tip-roll was reduced by 50%
    2. Over 90% of spray pattern fell within 70 ft. of C/L
    3. Test blocks indicated that pattern was regular, no streaks
    4. Size of droplets averaged between 0.01 cm$^2$ and 0.02 cm$^2$
    5. An exact count of droplets and finds was taken from test blocks.
  F. End of flight runs.

After test runs were completed, all test papers (each prox. 16 sq. in.) were divided into sections of 1 sq. in. Count and average was taken of each of the following test blocks. Wind was from south—left to right, flight from east to west.

I. 8 ft. downwind from C/L of flight.
  A. Panel 24, Clear Water Used
    1. Total drop count: 144
    2. Average drops per sq. in.: 9
  B. Panel 24, Water and poly(ethylene oxide)
    1. Total drop count: 241
    2. Average drops per sq. in.: 16
  C. Note: In path, 60% more droplets with drift control II. 20 ft. downwind from C/L of flight
  A. Panel 19, Clear Water Used
    1. Total drop count: 252.00
    2. Average drops per sq. in.: 15.75
  B. Panel 19, Water and poly(ethylene oxide)
    1. Total drop count: 195.00
    2. Average drops per sq. in.: 12.19

III. 42 ft. downwind from C/L of flight
  A. Panel 9, Clear Water Used
    1. Total drop count: 251.00
    2. Average drops per sq. in.: 15.69
  B. Panel 9, Water and poly(ethylene oxide)
    1. Total drop count: 107.00
    2. Average drops per sq. in.: 8.92

IV. 88 ft. downwind from C/L of flight
  A. Panel 2, Clear Water Used
    1. Total drop count: 102.00
    2. Average drops per sq. in.: 6.38
  B. Panel 2, Water and poly(ethylene oxide)
    1. Total drop count: 26.00
    2. Average drops per sq. in.: 1.63

C. Note: Water drop count was 4 times as great without drift control additive

V. 56 ft. upwind from C/L of flight
  A. Panel 5 LC, Clear Water Used
    1. Total drop count: 16.00
    2. Average drops per sq. in.: 1.00
  B. Panel 5 LC, Water and poly(ethylene oxide)
    1. Total drop count: 234.00
    2. Average drops per sq. in.: 14.63
  C. Note: At 56 ft. upwind from C/L of flight there was 14.63 times droplets per sq. in. more with drift control than when plain water was used.

It is therefore apparent that the present invention in the range of concentration of polyethylene oxide to water for use as a drift influencing composition, as disclosed herein, is one well adapted to attain all of the objects and advantages hereinabove set forth, together with other advantages which will become obvious and inherent from a description of the apparatus itself. It will be understood that certain combinations and subcombinations are of utility and may be employed without reference to other features and subcombinations. This is contemplated by and is within the scope of the present invention.

As many possible embodiments may be made of this invention without departing from the spirit or scope thereof, it is to be understood that all matters hereinabove set forth or shown in the accompanying drawings are to be interpreted as illustrative and not in any limiting sense.

I claim:

1. An agricultural composition for restricting the drift of agricultural insecticides and other chemicals sprayed onto crops from an aircraft comprising an aqueous solution of:
  (a) an agricultural insecticide or chemical in an agriculturally effective amount, and
  (b) from about seventy (70) to about two hundred (200) p.p.m. of polyethylene oxide to water and to water and having a molecular weight of 300,000 to about 4,000,000 by weight.

2. An agricultural composition for enhancing the drift of agricultural insecticides or other chemicals sprayed from an aircraft comprising an aqueous solution of:
  (a) an agricultural insecticide or other chemical in an agriculturally effective amount, and
  (b) from about ½ to about 70 p.p.m. of polyethylene oxide to water and having a molecular weight of about 300,000 to about 4,000,000 by weight.

3. In a method of restricting the drift of agricultural insecticides and other chemicals sprayed onto crops from an aircraft comprising the steps of:
  (a) selecting a polyethylene oxide having a molecular weight of about in the range of 300,000 to 4,000,000,
  (b) preparing an aqueous solution of said agricultural insecticide or other chemical which comprises said polyethylene oxide in water wherein the concentration is in the range of about 70 to 200 parts per million (p.p.m.), by weight, of said polyethylene oxide to said water,
  (c) spraying said aqueous solution from an airplane onto a crop to obtain superior deposition on the crop and wettability of the leaves thereof.

4. In a method for enhancing the drift of agricultural insecticides or other chemicals from an aircraft comprising the steps of:
  (a) selecting a polyethylene oxide (p.e.o.) having a molecular weight of about 300,000, to 4,000,000,
  (b) preparing an aqueous solution of said chemicals which comprises said polyethylene oxide in water wherein the concentration is in the range of about ½ to 70 parts per million, by weight of P.E.O. to said water,
  (c) spraying said aqueous solution from an airplane to obtain enhanced distribution and wettability on the surface sprayed.

* * * * *